(12) United States Patent
Meeks et al.

(10) Patent No.: US 7,532,318 B2
(45) Date of Patent: May 12, 2009

(54) WAFER EDGE INSPECTION

(75) Inventors: Steven W. Meeks, Fremont, CA (US);
Rusmin Kudinar, Fremont, CA (US);
William R. Wheeler, Saratoga, CA (US);
Hung Phi Nguyen, Santa Clara, CA (US); Vamsi Velidandla, San Jose, CA (US); Anoop Somanchi, Fremont, CA (US); Ronny Soetarman, Fremont, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 11/560,477

(22) Filed: Nov. 16, 2006

(65) Prior Publication Data

US 2007/0127016 A1 Jun. 7, 2007

Related U.S. Application Data

(63) Continuation of application No. 11/365,221, filed on Mar. 1, 2006, now Pat. No. 7,161,669, which is a continuation-in-part of application No. 11/196,540, filed on Aug. 3, 2005, now Pat. No. 7,161,668, which is a continuation-in-part of application No. 11/123,913, filed on May 6, 2005, now Pat. No. 7,161,667.

(51) Int. Cl.
*G01N 21/00* (2006.01)

(52) U.S. Cl. .................. 356/237.2; 356/237.1

(58) Field of Classification Search ........... 356/501, 356/496–499, 508, 614–620; 250/338.3, 250/559.29, 231.13–231.23, 237 R, 237 G, 250/232–236
See application file for complete search history.

(56) References Cited

U.S. PATENT DOCUMENTS

| | | | |
|---|---|---|---|
| 2,593,189 A | 4/1952 | Rinia | |
| 4,378,159 A | 3/1983 | Galbraith | |
| 4,585,348 A | 4/1986 | Chastang | |
| 4,601,575 A | 7/1986 | Tamaki | |
| 4,650,333 A | 3/1987 | Crabb | |
| 4,794,264 A | 12/1988 | Quackenbos et al. | |
| 4,851,276 A | 7/1989 | Kitahata et al. | |
| 4,870,631 A | 9/1989 | Stoddard | |
| 4,873,430 A | 10/1989 | Juliana | |
| 4,905,311 A | 2/1990 | Hino et al. | |
| 4,999,510 A | 3/1991 | Hayano | |
| 5,017,012 A | 5/1991 | Merritt, Jr. et al. | |
| 5,067,817 A | 11/1991 | Glenn | |

(Continued)

FOREIGN PATENT DOCUMENTS

DE 4105192 8/1991

(Continued)

*Primary Examiner*—Gregory J Toatley, Jr.
*Assistant Examiner*—Tri T Ton
(74) *Attorney, Agent, or Firm*—Luedeka, Neely & Graham, P.C.

(57) ABSTRACT

In one embodiment, a system to measure defects on a surface of a wafer and an edge of the wafer using a single tool comprises a radial motor to move an optical head in a radial direction to detect defects at locations displaced from the edge of the wafer, and a rotational motor to rotate the optical head around the edge of the wafer to detect defects on the edge of the wafer.

29 Claims, 13 Drawing Sheets

U.S. PATENT DOCUMENTS

| | | | |
|---|---|---|---|
| 5,125,741 A | 6/1992 | Okada | |
| 5,168,386 A | 12/1992 | Galbraith | |
| 5,189,481 A | 2/1993 | Jann | |
| 5,270,794 A | 12/1993 | Tsuji | |
| 5,392,116 A | 2/1995 | Makosh | |
| 5,416,594 A | 5/1995 | Gross | |
| 5,565,979 A | 10/1996 | Gross | |
| 5,604,585 A | 2/1997 | Johnson et al. | |
| 5,608,527 A | 3/1997 | Valliant et al. | |
| 5,610,897 A | 3/1997 | Yamamoto | |
| 5,633,747 A | 5/1997 | Nikoonahad | |
| 5,644,562 A | 7/1997 | de Groot | |
| 5,737,085 A | 4/1998 | Zollars et al. | |
| 5,798,829 A | 8/1998 | Vurens | |
| 5,864,394 A | 1/1999 | Jordan | |
| 5,880,838 A | 3/1999 | Marx | |
| 5,883,714 A | 3/1999 | Jann et al. | |
| 5,898,500 A | 4/1999 | Canteloup et al. | |
| 5,903,342 A | 5/1999 | Yatsugake | |
| 5,963,314 A | 10/1999 | Worster et al. | |
| 5,985,689 A | 11/1999 | Singhal | |
| 5,986,763 A | 11/1999 | Inoue | |
| 5,995,226 A | 11/1999 | Abe | |
| 6,020,966 A | 2/2000 | Ausschnitt et al. | |
| 6,031,615 A | 2/2000 | Meeks | |
| 6,081,325 A | 6/2000 | Leslie | |
| 6,091,493 A | 7/2000 | Stover et al. | |
| 6,122,046 A | 9/2000 | Almogy | |
| 6,130,749 A | 10/2000 | Meeks | |
| 6,154,280 A | 11/2000 | Borden | |
| 6,169,601 B1 | 1/2001 | Eremin et al. | |
| 6,172,752 B1 | 1/2001 | Haruna et al. | |
| 6,198,533 B1 | 3/2001 | Meeks | |
| 6,229,610 B1 | 5/2001 | Meeks | |
| 6,268,919 B1 | 7/2001 | Meeks | |
| 6,392,749 B1 | 5/2002 | Meeks | |
| 6,433,877 B2 | 8/2002 | Watanabe et al. | |
| 6,498,697 B1 | 12/2002 | Klimovitsky et al. | |
| 6,509,577 B1 * | 1/2003 | Babikian et al. | 250/559.36 |
| 6,515,745 B2 | 2/2003 | Vurens et al. | |
| 6,556,290 B2 | 4/2003 | Maeda et al. | |
| 6,603,541 B2 | 8/2003 | Lange | |
| 6,617,603 B2 | 9/2003 | Ishiguro et al. | |
| 6,624,884 B1 | 9/2003 | Imaino | |
| 6,624,894 B2 | 9/2003 | Olszak et al. | |
| 6,665,078 B1 | 12/2003 | Meeks | |
| 6,678,046 B2 | 1/2004 | Opsal | |
| 6,687,008 B1 | 2/2004 | Peale | |
| 6,690,473 B1 | 2/2004 | Stanke et al. | |
| 6,704,435 B1 | 3/2004 | Imaino | |
| 6,717,671 B1 | 4/2004 | Meeks | |
| 6,751,044 B1 | 6/2004 | Meeks | |
| 6,757,056 B1 | 6/2004 | Meeks | |
| 6,781,103 B1 | 8/2004 | Lane | |
| 6,804,003 B1 | 10/2004 | Wang et al. | |
| 6,813,034 B2 | 11/2004 | Rosencwaig et al. | |
| 6,917,433 B2 | 7/2005 | Levy et al. | |
| 6,940,609 B2 | 9/2005 | Scheiner | |
| 6,956,660 B2 | 10/2005 | Meeks et al. | |
| 7,019,850 B2 | 3/2006 | Finarov | |
| 7,023,547 B2 | 4/2006 | Venkatasubbarao et al. | |
| 7,042,556 B1 | 5/2006 | Sun | |
| 7,042,577 B1 | 5/2006 | Jacob et al. | |
| 7,046,352 B1 | 5/2006 | Dayal et al. | |
| 7,075,630 B2 | 7/2006 | Meeks | |
| 7,113,284 B1 | 9/2006 | Meeks | |
| 7,161,683 B2 | 1/2007 | Weitzel | |
| 2002/0015146 A1 | 2/2002 | Meeks | |
| 2002/0107650 A1 | 8/2002 | Wack et al. | |
| 2002/0118359 A1 | 8/2002 | Fairley | |
| 2002/0145740 A1 | 10/2002 | Meeks | |
| 2002/0163634 A1 | 11/2002 | Meeks | |
| 2003/0025905 A1 | 2/2003 | Meeks | |
| 2003/0179370 A1 | 9/2003 | Goldberg et al. | |
| 2003/0197874 A1 * | 10/2003 | Moghaddam et al. | 356/630 |
| 2004/0017561 A1 | 1/2004 | Meeks | |
| 2004/0046959 A1 | 3/2004 | Meeks | |
| 2004/0130710 A1 | 7/2004 | Hwang et al. | |
| 2004/0160604 A1 | 8/2004 | Meeks | |
| 2004/0169850 A1 | 9/2004 | Meeks | |
| 2004/0233419 A1 | 11/2004 | Meeks | |
| 2005/0023491 A1 | 2/2005 | Young | |
| 2005/0057747 A1 | 3/2005 | Meeks | |
| 2005/0206888 A1 | 9/2005 | Yoshida et al. | |
| 2006/0072106 A1 | 4/2006 | Matsui et al. | |
| 2007/0030493 A1 | 2/2007 | Zettler et al. | |

FOREIGN PATENT DOCUMENTS

| | | |
|---|---|---|
| EP | 0080540 | 6/1983 |
| GB | 725188 | 3/1955 |
| JP | 03085514 | 4/1991 |
| JP | 07055702 | 3/1995 |
| JP | 10325711 | 12/1998 |
| WO | WO9416310 | 7/1994 |

* cited by examiner

WAFER EDGE INSPECTION

RELATED APPLICATIONS

This application is a continuation of U.S. patent application Ser. No. 11/365,221 filed Mar. 1, 2006, now U.S. Pat. No. 7,161,669, entitled Wafer Edge Inspection, which is continuation-in-part of U.S. patent application Ser. No. 11/196,540 filed Aug. 3, 2005, now U.S. Pat. No. 7,161,668, entitled Wafer Edge Inspection, which is a continuation-in-part of U.S. patent application Ser. No. 11/123,913 filed May 6, 2005, now U.S. Pat. No. 7,161,667, entitled Wafer Edge Inspection, the disclosures of which are incorporated herein by reference.

BACKGROUND

The subject matter described herein relates to surface inspection techniques, and more particularly to wafer edge inspection.

Semiconductor materials may be inspected for defects such as, e.g., surface imperfections, particles, irregularities in the thickness of thin film coatings, and the like, which may hamper the performance of the semiconductor material. Some existing inspection systems direct a beam of radiation on the surface of the semiconductor material, then collect and analyze light reflected and/or scattered from the surface to quantify characteristics of the surface. Additional inspection techniques are desirable. In particular, it is desirable to inspect the edge or near edge of semiconductor wafers, compound semiconductor wafers, transparent wafers or thin film disks for defects.

BRIEF DESCRIPTION OF THE DRAWINGS

The detailed description is described with reference to the accompanying figures.

DETAILED DESCRIPTION

Described herein are exemplary systems and methods for wafer edge inspection. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

Figure 1:
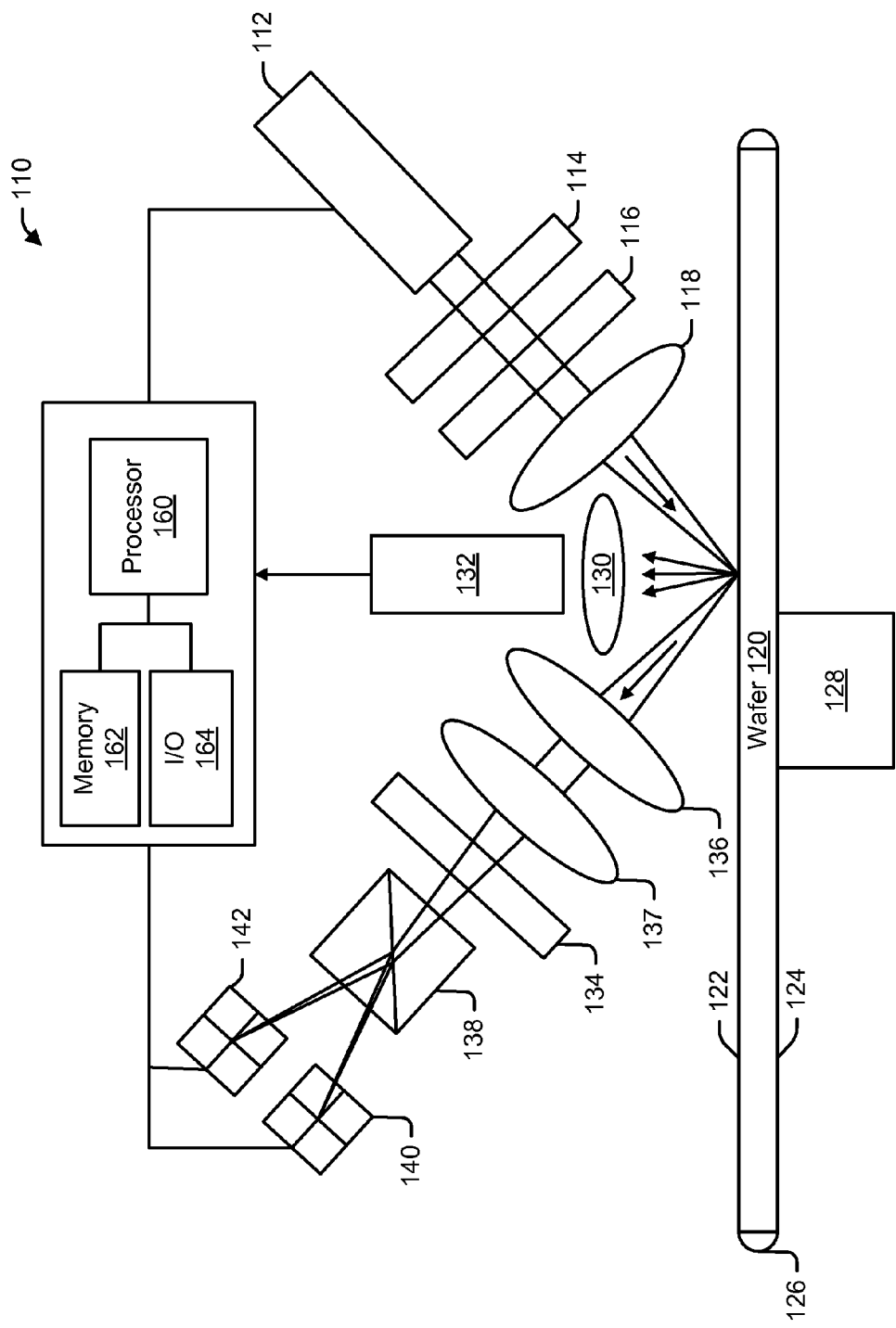
FIG. 1 is a schematic illustration of various optical components of an embodiment of an apparatus for wafer edge inspection.

FIG. 1 is a schematic illustration of one embodiment of an apparatus for wafer or disk edge inspection. Various optical testing components and techniques for surface inspection are described in U.S. Pat. Nos. 6,665,078, 6,717,671, 6,757,056, 6,268,919, 6,229,610, and 6,130,749 to Meeks, et al., the disclosures of which are incorporated herein by reference in their entirety. Any of the assemblies and techniques described in these patents may be used in a surface analyzer for wafer edge inspection.

One embodiment is adapted to perform film thickness measurements, surface roughness measurement, reflectivity measurement, magnetic imaging, and optical profiling using radiation in the optical spectrum. In alternate embodiments radiation outside the visible optical spectrum may be used. More particularly, FIG. 1 depicts an optics assembly capable of performing that includes a combined reflectometer, scatterometer, phase shift microscope, magneto-optic Kerr effect microscope and optical profilometer. This embodiment is capable of detecting and classifying a wide variety of defects at a wafer or disk edge or near edge.

Wafer 120 includes an upper surface 122, a lower surface 124, and an edge surface 126, which may be substantially flat or curved when viewed in a cross-sectional profile. In the embodiment depicted in FIG. 1, the wafer edge surface is curved when viewed in cross-sectional profile.

A surface analyzer assembly 110 is positioned to direct radiation onto a surface of wafer 120. In the embodiment depicted in FIG. 1, surface analyzer assembly 110 includes a laser diode 112, an optional polarizer 114, an optional half-wave plate 116, and a focusing lens 118 for directing radiation onto a surface of wafer 120. These components target radiation from the laser diode onto the surface of wafer 120, and hence may be considered a radiation targeting assembly. In alternative embodiment polarizer 114 and half-wave plate 116 may be omitted.

Surface analyzer assembly 110 further includes a collecting lens 130 and a photomultiplier tube (PMT) 132. These components collect radiation scattered by the surface of the wafer 120, and hence may be considered a scattered radiation assembly. In alterative embodiments the PMT 132 and collecting lens 130 may be replaced with an integrating sphere or an ellipsoidal mirror together with a PIN photodiode or avalanche photodiode.

Surface analyzer assembly 110 further includes a collimating lens 136, a wobble reduction lens 137, a quarter wave plate 134, a Wollaston prism 138 rotated at 45 degrees to the plane of incidence, and two quadrant detectors 140, 142 available from Hamamatsu, Inc. In another embodiment detectors 140, and 142 may be PIN photodetectors also available from Hamamatsu, Inc. The embodiment shown in FIG. 1 utilizes quadrant detectors so that the slope of the surface may be measured. The surface slope may be integrated to produce the surface profile. These components collect radiation reflected from the surface of wafer 120, and hence may be considered a reflected radiation assembly. The wobble reduction lens 137 is a converging lens. In alternative embodiments the wobble reduction lens 137 and the collimating lens 136 may be combined into a single lens. The wobble reduction lens is chosen so that its focal length is substantially equal to the distance between wobble reduction lens 137 and the quadrant detectors 140 and 142. When this is done the surface slope measured at the quadrant detectors will be minimized. That is, the system will be most tolerant of wobble of the wafer. Another embodiment would position the detectors 140 and 142 at a distance slightly longer or shorter than the focal length of the wobble reduction lens 137. In this case the system would have some sensitivity to both wafer wobble and to surface slope.

In one embodiment surface analyzer assembly 110 uses a multi-mode, multi-wavelength laser diode 112 which is available from Rohm Co., LTD Kyoto, Japan as model number RLD-78MV and a polarizer 114 which is adjusted for P polarization and improves the extinction ratio of the laser. The radiation may be of any wavelength. In one embodiment a 405 nm violet source available from Coherent, Inc may be implemented. In another embodiment a 635 nm source may be implemented. The mechanically rotatable half wave plate 116 is available from CVI Laser Corp. and can be used to rotate the polarization between 45 degrees, and P or S polarization's. The half wave plate may be replaced with a quarter wave plate which is rotated at 45 degrees to the incident polarization. This will result in circular polarization incident upon the wafer. A quarter wave plate which is rotated at angles other than 45 degrees to the incident polarization will result in elliptical polarization incident upon the wafer. Alternative techniques for rotating the polarization include rotating the laser diode 112 or to use a liquid crystal polarization rotator such as model LPR-100 available from Meadowlark Optics, Frederick, Colo. The latter embodiment has the advantage of being a purely electronic means of polarization rotation and as a result there is no possibility of beam movement when the polarization is rotated.

Focusing lens 118 creates a small spot on the surface of a wafer 120. The PMT 132 and collecting lens 130 are used to measure the scattered light for the purposes of computing the surface roughness, measuring debris, detecting stains, cracks, scratches, delaminations, blisters or corrosion on the disk or wafer 120 surface or edge 126 or near edge regions.

After reflecting from the disk, the beam passes through the collimating lens 136, the wobble reduction lens 137, and a quarter-wave plate 134. The beam is then polarization split with a Wollaston prism 138 available from CVI Laser Corp., for example, and each polarization component is detected with separate photodetectors 140, 142. The plane of the Wollaston prism (the plane of the S and P components) may be adjusted at substantially 45 degrees to the plane of incidence. The first mixed component of the beam (which includes both P and S components with respect to the plane of incidence) is directed to a detector 140 and the second mixed component (which includes both P and S components with respect to the plane of incidence) is directed to a second detector 142. In one embodiment the photodetectors 140, 142 may have a diffuser placed in front of them to reduce the residual position sensitivity of the photodiodes. The difference between the intensity measured by the photodetectors is proportional to the cosine of the phase difference between the first and second mixed components coming from the Wollaston prism. As a result this instrument can get different types of information when used in different modes.

When the polarization is adjusted to P, the P specular and P scattered light is measured resulting in sensitive measurements of carbon thickness (or any simple layer thickness) and carbon wear. The P specular signal is obtained by rotating the half wave plate 116 so that the polarization output from the half wave plate is P polarized. The P specular signal is given by the sum of the signal from detectors 140 and 142. When the polarization is adjusted to 45 degrees (exactly between P and S polarization) the instrument is most sensitive to measurements of the phase change induced by changes in the thickness of the thin films on the disk or wafer surface. In the phase shift mode the instrument measures lubricant, carbon, or other film thickness changes on thin film disks or wafers. The phase shift is measured by taking the difference between the signals measured at detectors 142 and 140. This gives an output that is proportional to the cosine of the phase difference between the first and second mixed components of the wave. The orientation of the quarter wave plate 134 is adjusted to optimize the sensitivity to lubricant, carbon wear, other film thickness changes or changes in phase due to the presence of defects. The individual components may also be measured; that is, the first and second mixed components of the 45 degrees polarized light. These are measured simultaneously with the phase shift and the scattered light.

When the half wave plate is rotated so that the polarization is adjusted to S polarization the instrument will be able to measure the S specular and the S scattered light and, as a result, obtain the surface roughness and other properties of the sample. The S specular signal is given by the sum of the signal from detector 140 and detector 142. The angle of incidence shown in FIG. 1 is 58 degrees but angles greater or less than 58 degrees will work as well. The longitudinal Kerr effect can be measured by operating the instrument in any of the linear polarization's, i.e., P, S or 45 degrees . Rotating the quarter wave plate 134 to achieve maximum sensitivity to the magnetic pattern optimizes the Kerr effect signal. The orientation of the quarter wave plate which optimizes the Kerr effect may be different from that which optimizes for lubricant and carbon sensitivity. As a result the quarter wave plate is made to be removable, for example, so that two different and separately optimized plates can be used for the different applications. A different embodiment would have a miniature motor to rotate the orientation of the quarter wave plate so as to optimize the signal for the Kerr effect, lubricant, carbon or defect detection mode. Different polarizations may require a different quarter wave plate adjustment to achieve optimization. When in this mode the instrument functions as a Kerr effect microscope. In one embodiment the S polarization is used to image the longitudinal Kerr effect. When the surface is imaged by the OSA in S linear polarization the reflected light has its polarization converted to elliptical polarization whose major axis is rotated depending upon the orientation of the magnetization upon the thin film disk. This Kerr effect signal is detected by measuring the two signals coming from the polarization beam splitter and subtracting them. This will give a signal whose sign is related to the direction of the magnetization and whose amplitude is proportion to the magnetization.

The data collected by the scattered radiation collection assembly and the reflected radiation collection assembly is fed to a processing module that includes a processor 160, a memory module 162, and an I/O module 164. Processor module comprises logic instructions that enable the instrument described in FIG. 1 to simultaneously measure the profile (height and depth) of the surface, the S and P components of the reflectivity, the phase shift between the P and S waves and the scattered light. It is also capable of measuring the Magneto-optic Kerr effect.

The measurement of the phase shift between the S and P components of the optical wave requires a means to stabilize the long-term phase drift of the diode laser. This can be accomplished by use of a reference mirror. A reference mirror may be embodied as a stable surface such as, e.g., a gold mirror, a section of a thin film disk, or section of a silicon wafer. The reference mirror may be calibrated when the instrument is first set up by measuring and recording the phase shift of the reference mirror. At times after the initial calibration of the instrument the reference mirror is measured prior to a measurement of the sample. Any deviation of the reference mirror reading from the initial reading is recorded and subtracted from the measurement of the sample readings. This insures that the phase shift reading from the surface under measurement will remain stable over time. The same procedure can also be applied to the measurement of the S specular and P specular signals. In this case when the instrument is calibrated the values of the P specular and S specular signals measured on the reference mirror are recorded and deviations from these values are used to correct the specular data. This removes any drift from the P and S specular signals.

The above discussion is relating to an instrument which has an angle of incidence that is near 60 degrees from the vertical. Similar ideas can be applied to a machine operating at angles less than or greater than 60 degrees. When the angle of incidence changes the interpretation of the various quadrants of the histogram will change.

Figure 2:
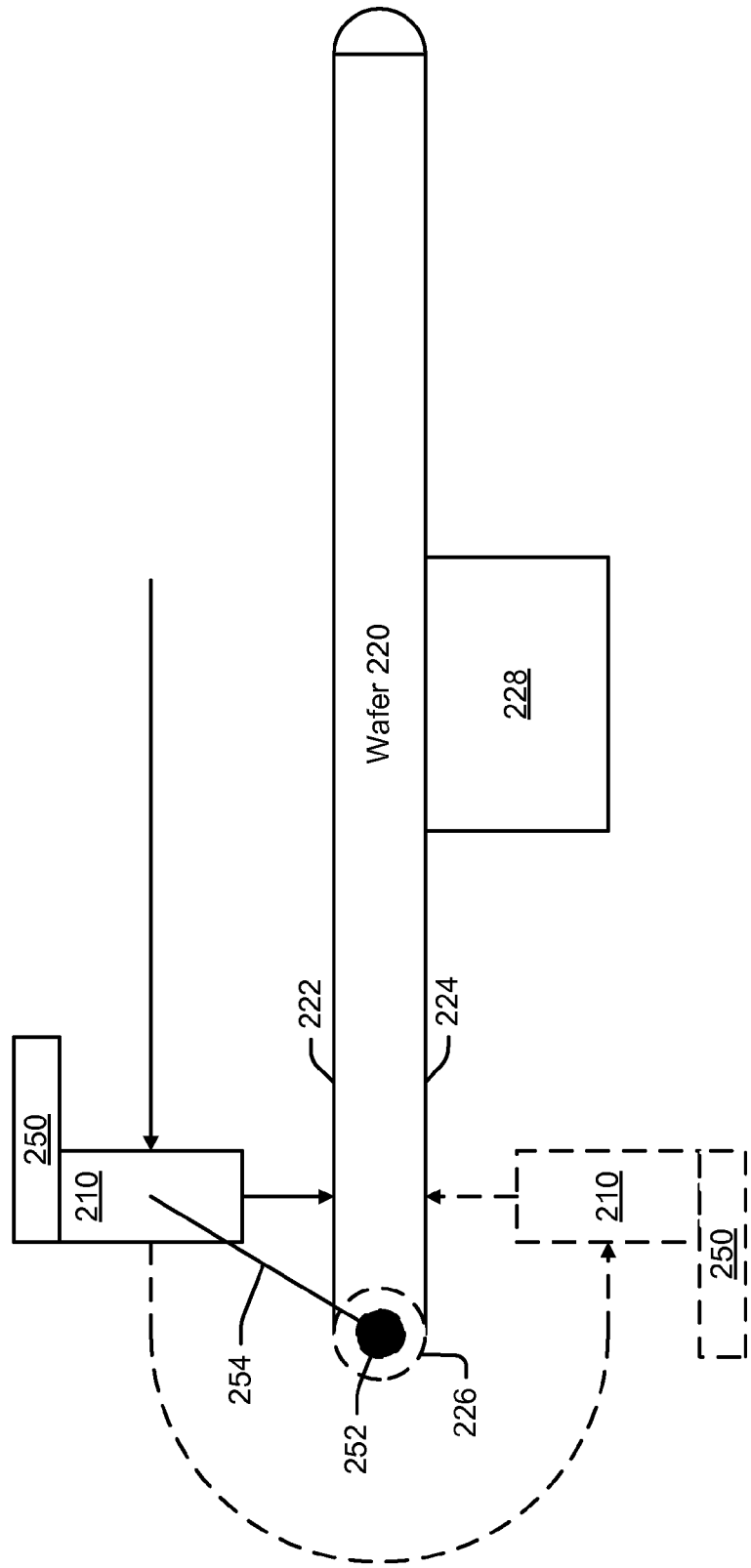
FIG. 2 is a schematic illustration of one embodiment of an apparatus for wafer edge inspection.

FIG. 2 is a schematic illustration of one embodiment of an apparatus for wafer edge inspection. During the inspection process a wafer 220 may be rotated about a central axis on a spindle 228, which may be connected to a suitable motor or other drive assembly for inducing rotational motion to the spindle. A first drive assembly including, e.g., a motor for moving the head in the horizontal direction 250 moves a surface analyzer assembly 210 as described herein or as described in U.S. Pat. Nos. 6,665,078, 6,717,671, 6,757,056, 6,268,919, 6,229,610, and 6,130,749 over the wafer surface, generating data about various characteristics of the surface. A second drive assembly including, e.g., a rotational motor connected to the surface analyzer assembly 210 by a suitable linkage 254 provides rotational motion to move the surface analyzer assembly 210 around the edge surface 226 of the wafer in a path illustrated by the dashed arrow in FIG. 2.

In one embodiment the motor producing the linear motion 250 and the rotational motor 252 cooperate to maintain a substantially fixed distance between the surface analyzer assembly 210 and the respective surfaces 222, 224, 226 of the wafer as the surface analyzer assembly 210 rotates about the edge surface 226 of the wafer. The edge of the wafer 226 is not necessarily in the shape of a semicircle but may in general be any type of shape. If motors 250 and 252 are operated in a cooperative manner then the head 210 may be kept at a fixed distance above the wafer edge regardless of the shape of the edge. Optionally, the motor producing the linear motion 250 can cause the surface analyzer assembly 210 to traverse the top 222 and or bottom surface 224 of wafer 220, permitting the surface 224 or 222 to be scanned for defects.

Figure 3:
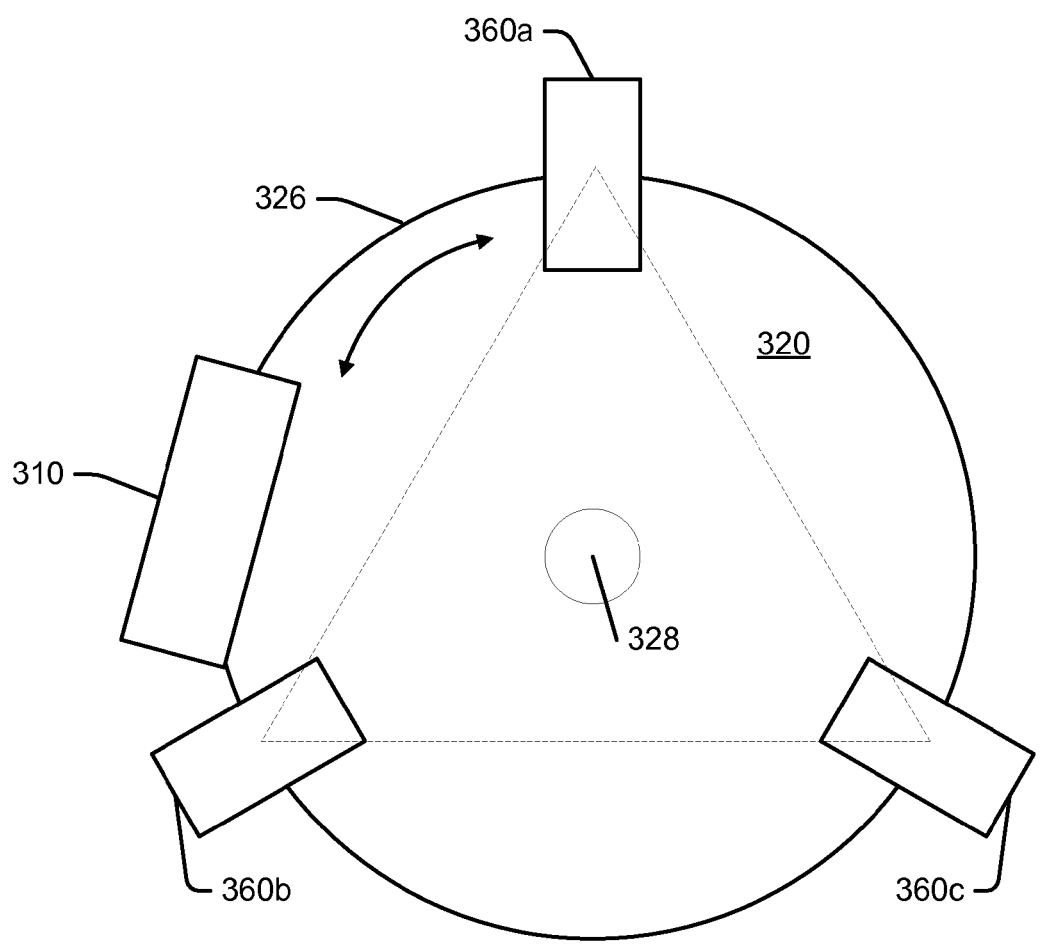
FIG. 3 is a schematic illustration of one embodiment of an apparatus for wafer edge inspection.

In one embodiment the apparatus comprises an assembly for centering the wafer on the spindle, which reduces the lateral variation (or "wobble") in the edge of the wafer as it rotates about a central axis. FIG. 3 is a schematic illustration of a wafer edge inspection system illustrating an assembly for centering the wafer 320. Referring to FIG. 3, a wafer 320 rotates about a central axis on a spindle 328. Wafer 320 may rotate in either direction, as illustrated by the dual-headed arrow. An surface analyzer assembly 310 scans the edge 326 of wafer 320, as described above.

Three positioning heads 360a, 360b, 360c are positioned adjacent three points on the outer edge 326 of wafer 320. In one embodiment the three positioning heads 360a, 360b, 360c are positioned at the respective vertices of an equilateral triangle circumscribed by the edge of wafer 320. However, the positioning heads 360a, 360b, 360c may be otherwise positioned.

The center of the triangle represented by positioning heads 360a, 360b, 360c corresponds to the center of the spindle 328. In one embodiment, the positioning heads 360a, 360b, 360c may be configured to transfer their (x, y) coordinates to the processing module (see, FIG. 1), which calculates the (x, y) coordinates of the center of the wafer 320. The wafer 320 may then be moved such that the center of the wafer 320 corresponds to the center of the spindle 328. In one embodiment, one or more of the positioning heads 360a, 360b, 360c includes a pushing mechanism such as, e.g., a servo-mechanical plunger to position the wafer 320 over the center of the spindle.

In one embodiment the positioning heads 360a, 360b, 360c are adapted to communicate their respective (x, y) coordinates to the processor 160, which calculates the (x, y) coordinates of the center of the wafer from the positions of the positioning heads. The processor then determines the amount of movement necessary to position the center of the wafer over the center of the spindle, and transmits instructions to the positioning heads to move the wafer 320. In another embodiment the wafer 320 and the positioning heads 360a, 360b, 360c remain fixed in position and the spindle 328 is moved.

In an alternate embodiment an apparatus for surface analysis may use multiple surface analyzer assemblies rather than rotating a single surface analyzer assembly around multiple surfaces of a wafer. For example, a first surface analyzer assembly may scan an upper surface of the wafer, while a second surface analyzer assembly may scan an edge surface of the wafer and a third surface analyzer may scan a lower surface of the wafer.

Figure 4:
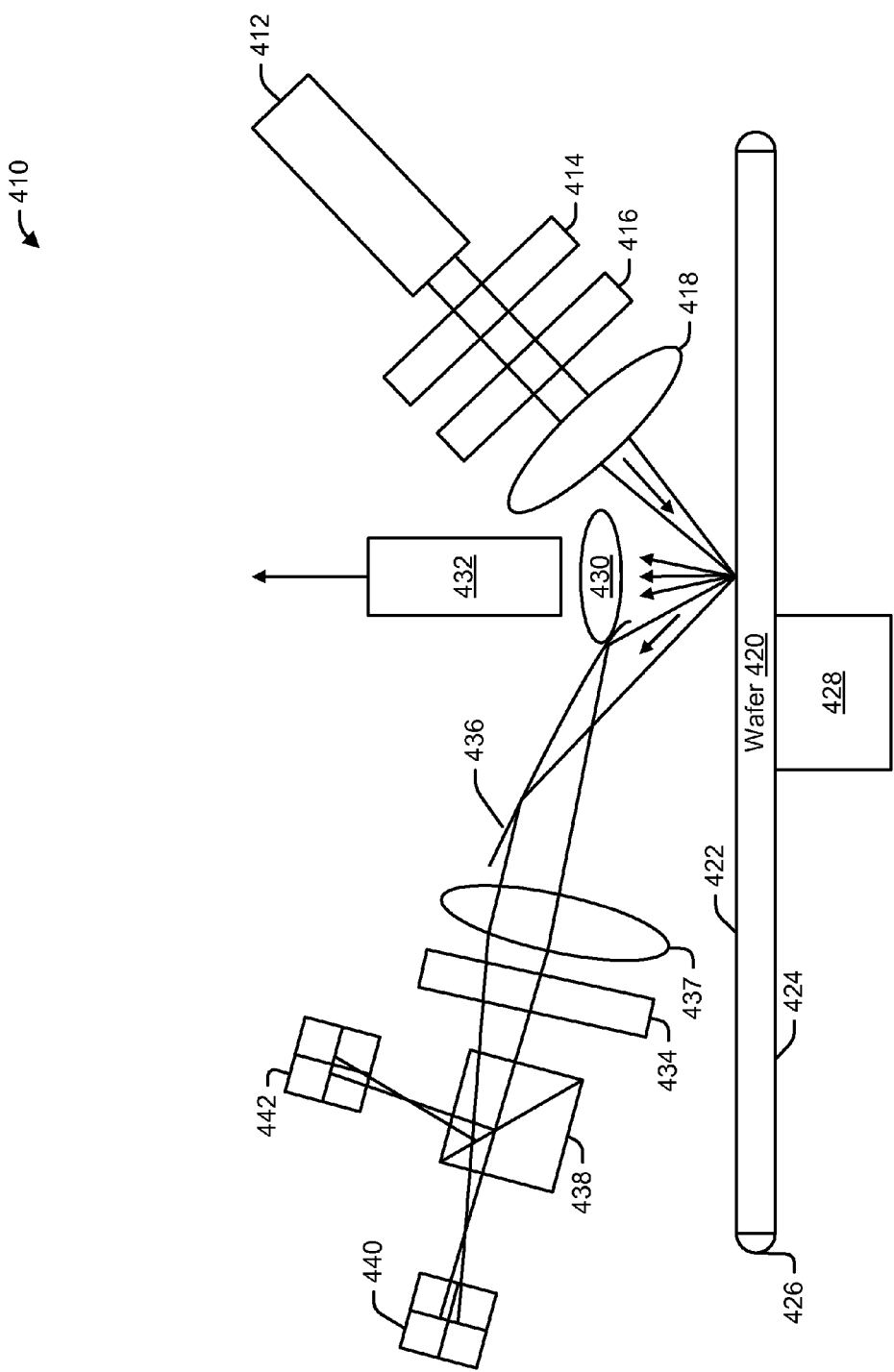
FIG. 4 is a schematic illustration of various optical components of an embodiment of an apparatus for wafer edge inspection.

FIG. 4 is a schematic illustration of various optical components of an embodiment of an apparatus for wafer edge inspection. Wafer 420 includes an upper surface 422, a lower surface 424, and an edge surface 426, which may be substantially flat or curved when viewed in a cross-sectional profile. In the embodiment depicted in FIG. 4, the wafer edge surface is curved when viewed in cross-sectional profile.

A surface analyzer assembly 410 is positioned to direct radiation onto a surface of wafer 420. In the embodiment depicted in FIG. 4, surface analyzer assembly 410 includes a laser diode 412, an optional polarizer 414, an optional half-wave plate 416, and a focusing lens 418 for directing radiation onto a surface of wafer 420. These components target radiation from the laser diode onto the surface of wafer 420, and hence may be considered a radiation targeting assembly. In an alternative embodiment polarizer 414 and half-wave plate 416 may be omitted.

Surface analyzer assembly 410 further includes a collecting lens 430 and a photomultiplier tube (PMT) 432. These components collect radiation scattered by the surface of the wafer 420, and hence may be considered a scattered radiation assembly. In alterative embodiments the PMT 432 and collecting lens 430 may be replaced with an integrating sphere or an ellipsoidal mirror together with a PIN photodiode or avalanche photodiode.

Surface analyzer assembly 410 further includes a reflecting mirror 436 to collect light reflected from the surface 422 of wafer 420. In one embodiment, reflecting mirror 436 may be implemented as a paraboloid reflector, e.g., a parabola of revolution. The paraboloid reflector 436 may be positioned such that its focus is approximately coincident with the focus of the laser and the axis of the paraboloid is tilted slightly to allow room for further optical components. Radiation reflected from paraboloid reflector 436 is collimated (i.e., divergence of the light rays is removed).

The collimated beam exiting the paraboloid reflector 436 can move up and down or from side to side (i.e., in and out of the page) due to the shape of the edge. Hence, light collected by the reflecting mirror 436 is directed to a wobble reduction lens 437. The wobble reduction lens 437 directs the collimated beam towards a fixed focus of the lens.

Radiation passing through the wobble reduction lens 437 is directed to a quarter wave plate 434, a polarizing beam splitter 438, and two quadrant detectors 440, 442. The polarizing beam splitter 438 may be a polarizing beam splitter cube, a Wollaston prism or some another suitable polarizing beam splitter. In another embodiment detectors 440, and 442 may be PIN photodetectors also available from Hamamatsu, Inc. These components collect radiation reflected from the surface of wafer 420, and hence may be considered a reflected radiation collection assembly.

In one embodiment, the detectors 440, 442 may be placed at or slightly behind the fixed focus of the wobble reduction lens 437. If the detectors are placed slightly behind or in front of the fixed focus of the anti-wobble lens, then a profile (topography) signal may be detected with the quad detectors.

In one embodiment, scattered light may be collected by removing a portion of the reflecting mirror 436 to the left of the focus and placing a PMT 432 (or avalanche photodiode or PIN photodiode) above this location. Optionally, a collecting lens 430 may be included.

Detectors 440, 442 and PMT 432 may have outputs connected to a processing module substantially as described in FIG. 1 to process the output substantially as described above.

Figure 5:
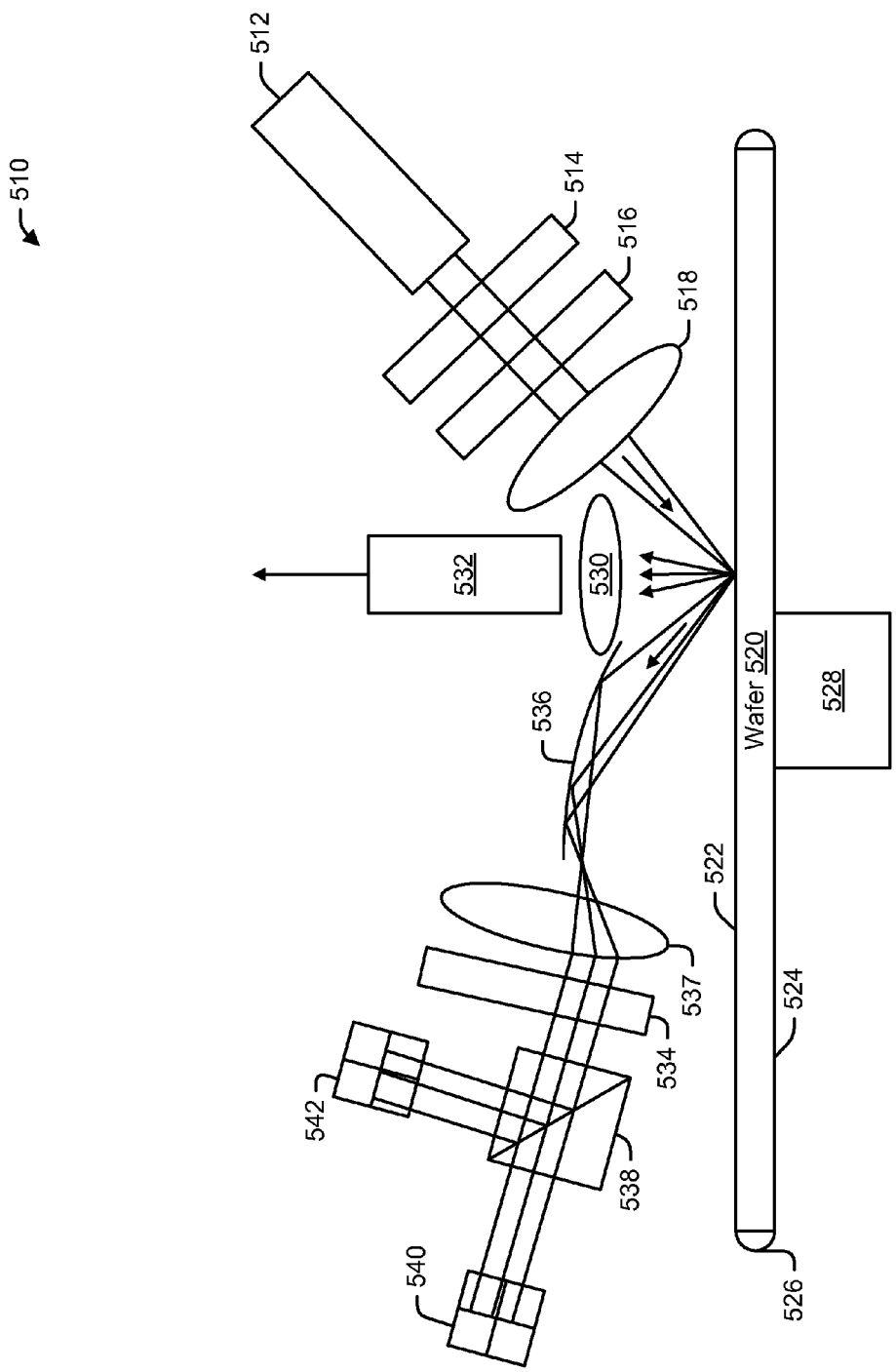
FIG. 5 is a schematic illustration of various optical components of an embodiment of an apparatus for wafer edge inspection.

FIG. 5 is a schematic illustration of various optical components of in an alternate embodiment of an apparatus for wafer edge inspection. A surface analyzer assembly 510 is positioned to direct radiation onto a surface of wafer 520. In the embodiment depicted in FIG. 5, surface analyzer assembly 510 includes a laser diode 512, an optional polarizer 514, an optional half-wave plate 516, and a focusing lens 518 for directing radiation onto a surface of wafer 520. These components target radiation from the laser diode onto the surface of wafer 520, and hence may be considered a radiation targeting assembly. In alternative embodiment polarizer 514 and half-wave plate 516 may be omitted.

Surface analyzer assembly 510 further includes a collecting lens 530 and a photomultiplier tube (PMT) 532. These components collect radiation scattered by the surface of the wafer 520, and hence may be considered a scattered radiation assembly. In alterative embodiments the PMT 532 and collecting lens 530 may be replaced with an integrating sphere or an ellipsoidal mirror together with a PIN photodiode or avalanche photodiode.

Surface analyzer assembly 510 further includes a reflecting mirror 536 to collect light reflected from the surfaces 522, 526, or 524 of wafer 520. In an embodiment, reflecting mirror 536 may be implemented as an ellipsoidal (that is, an ellipse of revolution) reflector. The ellipsoidal reflector 536 may be positioned such that its first focus is approximately coincident with the focus of the laser and the axis of the ellipsoid is tilted slightly to allow room for further optical components. Radiation reflected from the ellipsoidal reflector 536 is directed to its second focal point between the reflector 536 and a collimating lens 537. The collimating lens 537 is placed one focal length from the second focus of the ellipsoidal mirror 536. In this manner the light exiting the collimating 537 lens will be collimated.

The collimated beam exiting the collimating lens 537 is directed to a quarter wave plate 534, a polarizing beam splitter 538, and two quadrant detectors 540, 542. The polarizing beam splitter 538 may be a polarizing beam splitter cube, a Wollaston prism or some another suitable polarizing beam splitter. In another embodiment detectors 540, and 542 may be PIN photodetectors also available from Hamamatsu, Inc. These components collect radiation reflected from the surface of wafer 520, and hence may be considered a reflected radiation collection assembly.

Detectors 540, 542 and PMT 532 may have outputs connected to a processing module substantially as described in FIG. 1 to process the output substantially as described above.

Figure 6:
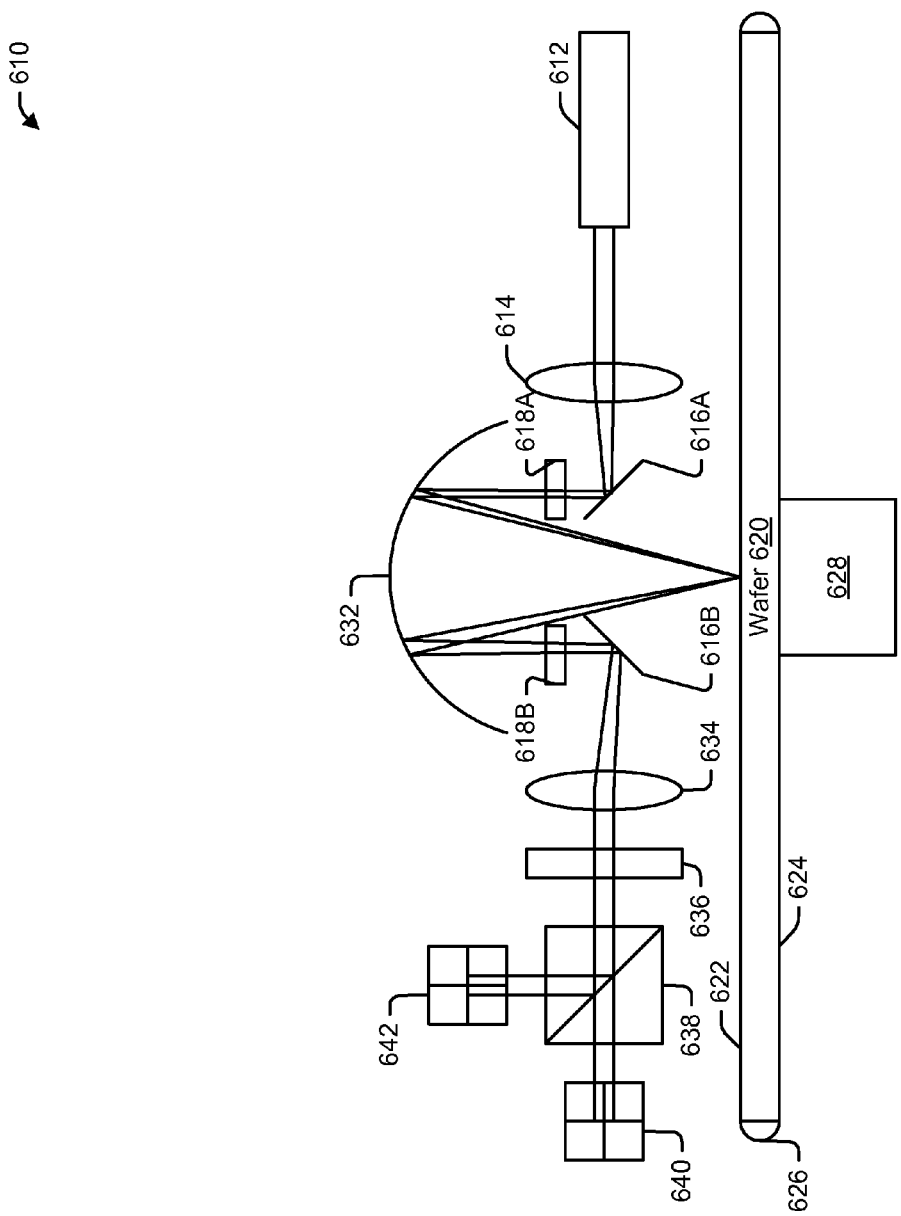
FIG. 6 is a schematic illustration of various optical components of an embodiment of an apparatus for wafer edge inspection.

FIG. 6 is a schematic illustration of various optical components of an embodiment of an apparatus for wafer edge inspection. Wafer 620 includes an upper surface 622, a lower surface 624, and an edge surface 626, which may be substantially flat or curved when viewed in a cross-sectional profile. In the embodiment depicted in FIG. 6, the wafer edge surface is curved when viewed in cross-sectional profile.

A surface analyzer assembly 610 is positioned to direct radiation onto a surface of wafer 620. In the embodiment depicted in FIG. 6, surface analyzer assembly 610 includes a laser diode 612 and a focusing lens 614 for directing radiation onto a surface of turning mirror 616A. Mirror 616A reflects light onto the surface of a spherical or hemispherical mirror 632. In one embodiment the radiation reflected from mirror 616A may pass through a Schmidt corrector plate 618A.

Radiation reflected from spherical mirror 632 is reflected onto the surface 622, and a portion of the radiation incident on surface 622 is reflected back to spherical mirror 632, which reflects the radiation onto turning mirror 616B. In one embodiment the radiation reflected from spherical mirror 632 onto mirror 616B may pass through a Schmidt corrector plate 618B.

Radiation reflected from turning mirror 616B passes through collimating lens 634, quarter-wave plate 636, and onto polarizing beam splitter 638 (which is rotated at 45 degrees to the plane of incidence), which directs the split beams onto detectors 640, 642. The polarizing beam splitter 638 may be a polarizing beam splitter cube, a Wollaston prism or some another suitable polarizing beam splitter. In another embodiment detectors 640, and 642 may be PIN photodetectors also available from Hamamatsu, Inc. These components collect radiation reflected from the surface of wafer 620, and hence may be considered a reflected radiation collection assembly.

In one embodiment, scattered light may be collected by removing a portion part of the spherical mirror 632, e.g., in the center of the spherical mirror, and placing a PMT (or avalanche photodiode or PIN photodiode) above this location. Optionally, a collecting lens may be included.

Figure 7:
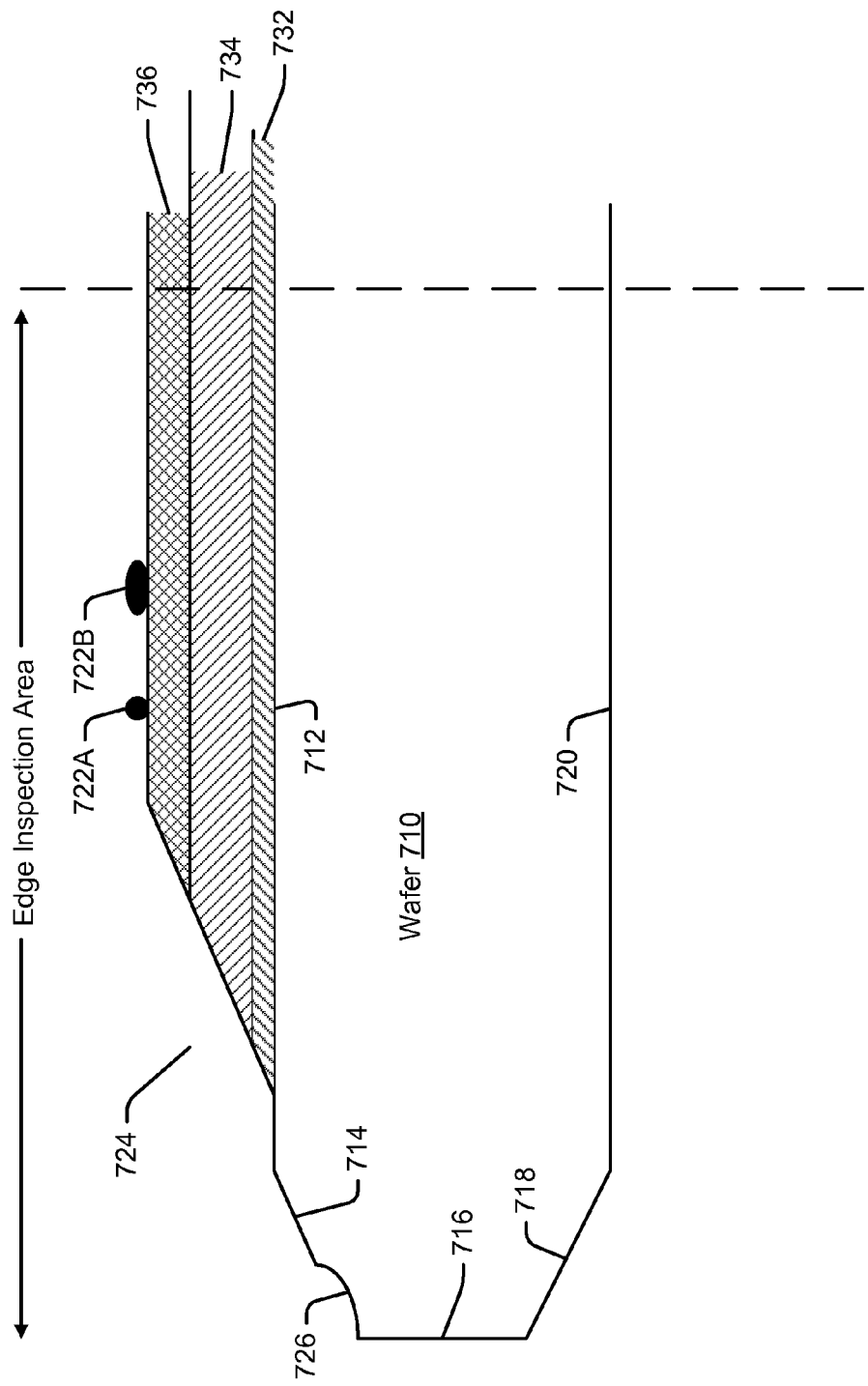
FIG. 7 is a schematic illustration of a wafer illustrating possible defects.

FIG. 7 is a schematic illustration of an edge inspection area of a wafer 710, which may correspond to wafers 220, 320 depicted in FIG. 2 and FIG. 3, respectively. The edge inspection area may be divided into five unique areas including a top near edge zone 712, a top bevel zone 714, an apex zone 716, a bottom bevel zone 718, and a bottom near edge zone 720. One or more layers of conductive, semi-conductive, or non-conductive materials 732, 734, 736 may be deposited on a surface 712 of the wafer 710.

FIG. 7 further depicts common defects that occur at or near the edge area of a wafer 710. Common defects may include debris particles 722A, 722B on the surface of wafer 710, undesired delaminations of the layers 732, 734, 736 on the surface 712 of the wafer 710, one or more chips or scratches 726 in the edges 714, 716, 718 or on the surfaces 712, 720 of wafer 710, or residue on the surfaces 712, 720 of the wafer 710.

In one embodiment a system and method for wafer edge inspection may scan the wafer edge to generate one or more files comprising data that represents one or more signals from radiation reflected from points on the surface of the wafer edge. The reflected radiation data may be analyzed to determine a background "noise" radiation level reflected from the surface, and one or more thresholds may be set in relation to the background noise level. Data points that fall outside the threshold may be marked as a defect. Defect regions may be further analyzed, classified, and reported.

Figure 8:
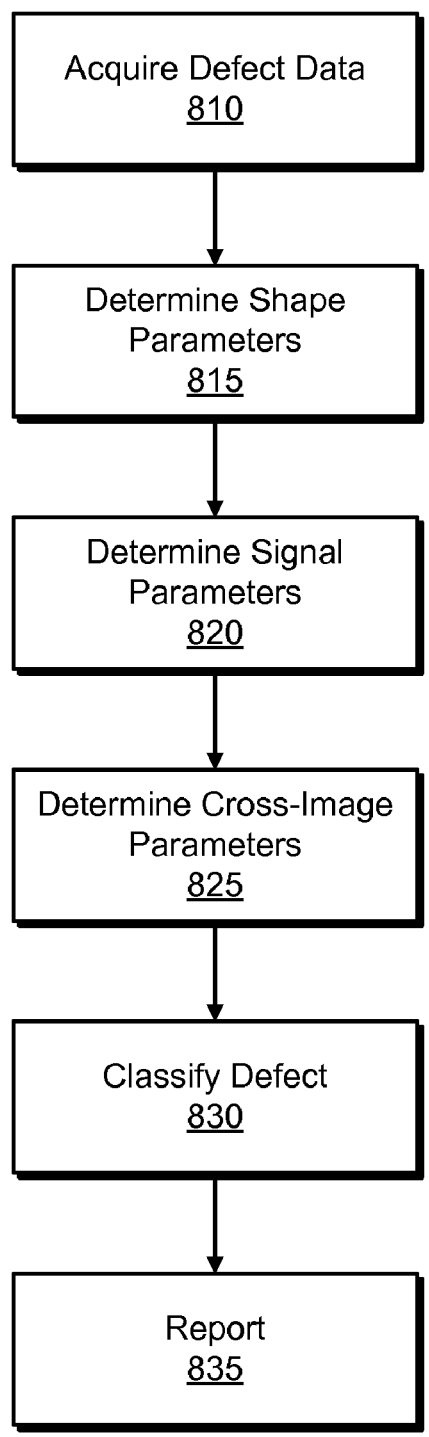
FIG. 8 is a flowchart illustrating operations in one embodiment of a method for wafer edge inspection.
Figure 9:
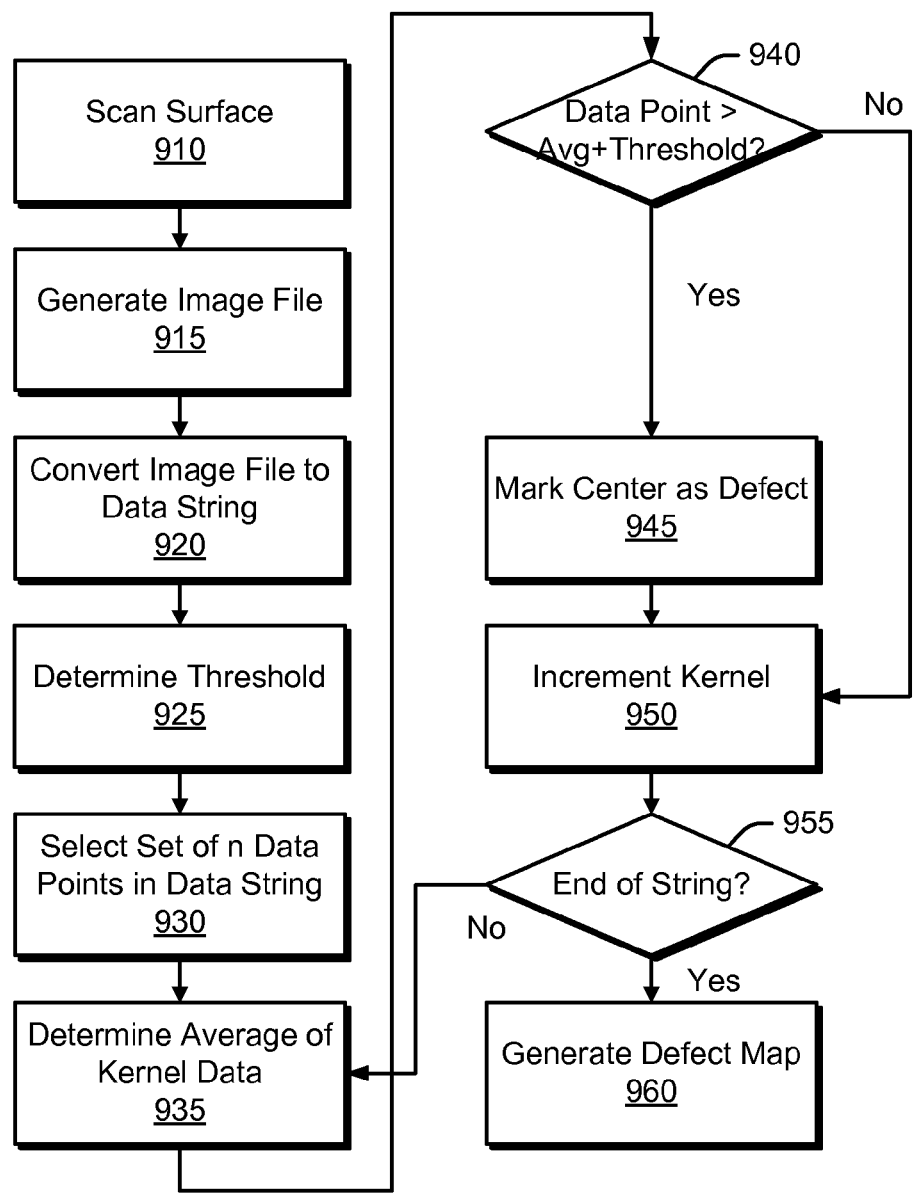
FIG. 9 is a flowchart illustrating operations in one embodiment of a method for acquiring defect data.
Figure 11:
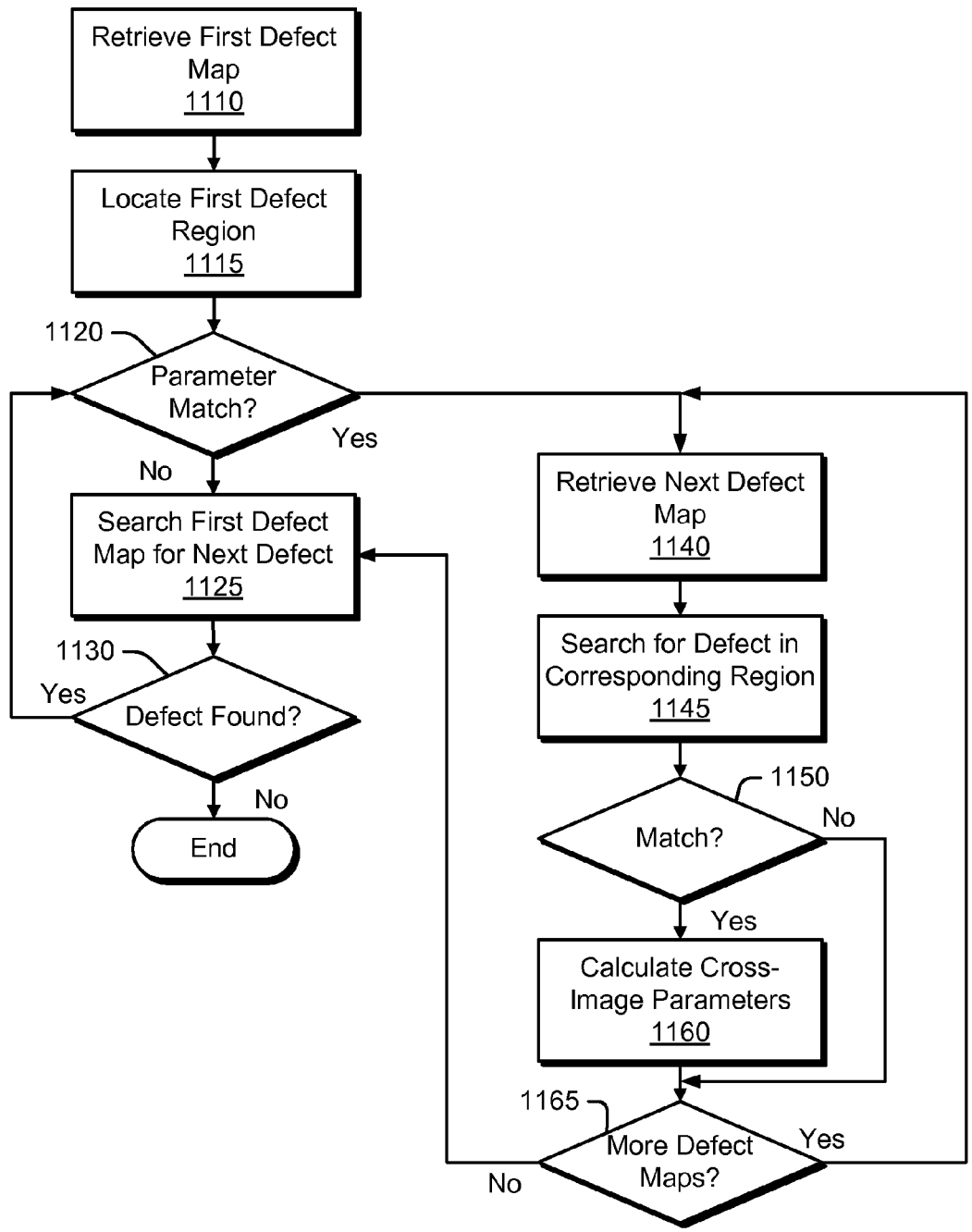
FIG. 11 is a flowchart illustrating operations in one embodiment of a method for determining cross-image parameters.

FIGS. 8-9 and 11 are flowcharts illustrating operations in a first embodiment of a method for wafer edge inspection. FIG. 8 is a flowchart illustrating high-level operations in one embodiment of a method for wafer edge inspection. In one embodiment, the operations illustrated in FIGS. 8-9 and 11 may be stored as logic instructions in a computer-readable medium such as the memory module 162 depicted in FIG. 1. The memory instructions, when executed by the processor 160, configure the processor to perform the operations depicted in FIGS. 8-9 and 11.

Referring to FIG. 8, at 810 defect data is acquired. FIG. 9 is a flowchart illustrating operations in one embodiment of a method for acquiring defect data (operation 810). Referring to FIG. 9, at operation 910 the surface of a wafer 710 is scanned. Defect data may be acquired by scanning the surface of a wafer 710 using a surface scanning assembly as described in FIGS. 1 and 4-6 herein. In one embodiment, the surface scanning assembly is rotated about the edge of the wafer 710 as depicted in FIG. 2. In one embodiment the surface scan may include scanning edge portions of the wafer such as, for example, edge portions 712, 714, 716, 718 and 720.

At operation 915 an image file is generated. In one embodiment, characteristics of radiation reflected from points on the surface of wafer 710 are recorded in a suitable memory such as e.g., a data file. In one embodiment, the data file may record data in a format of an array of pixels, each representing a point on the surface of the wafer 710. One or more characteristics of the radiation reflected from the surface are recorded in association with the pixel. In one embodiment the characteristics may include intensity measurements, reflectance percentages, phase information, or the like. At operation 915 the image file may be converted to a data string.

At operation 925 one or more thresholds for the characteristics of the radiation reflected from the surface are determined. The threshold(s) may be used to locate data in the image file that represents a defect on the surface of wafer 710. In one embodiment, threshold(s) may be determined by calculating an average (or median) level of the reflected radiation characteristic from a portion of the surface of wafer 710. In one embodiment, an average (or median) value may be computed using the entire data file. In another embodiment, an average (or median) value may be computed using a subset of the data file. The average (or median) value represents the "noise" level in reflected radiation.

In one embodiment, the threshold may be determined as a fixed percentage of the average (or median) value of the reflected radiation characteristic. In another embodiment, the threshold may be determined as a fixed percentage of the range in the reflected radiation characteristic. Other threshold measures may be implemented. In one embodiment, both upper and lower thresholds may be established.

Radiation reflection characteristics may be compared to the upper and lower thresholds as part of a technique to detect defects on the surface of wafer 710. In one embodiment, the reflectance data associated with each pixel may be compared with the threshold(s).

In an alternate embodiment a data averaging technique may be implemented to smooth fluctuations in the data that may give erroneous results. For example, at operation a set of n adjacent data points in the data set, referred to herein as a kernel. The number n may be selected such that the kernel length represents a physical distance on the surface of wafer 710 that exceeds the anticipated size of the largest defect of interest. For example, if the anticipated size of the largest defect is 100 micrometers, then the kernel size may be set to include a number of pixels that extends greater than 100 micrometers across the surface of wafer 710.

An average (or median) of the reflectance data associated with the points in the kernel may be computed. In one embodiment, a pixel may be considered to represent a defect if the reflectance data associated with the pixel exceeds the sum of the threshold and the average (or median) of the reflectance data associated with the points in the kernel. By contrast, a pixel may be considered not to represent a defect if the reflectance data associated with the pixel fails to exceed the sum of the threshold and the average (or median) of the reflectance data associated with the points in the kernel. In one embodiment, the pixel that represents the center point of the kernel may be compared.

Hence, if, at operation 940, the reflectance data associated with the data point in the kernel exceeds the sum of the average of the data points in the kernel and the threshold, then control passes to operation 945 and the data point may be marked as a defect, and the defect status of the may be recorded in the image file. Control then passes to operation 950 and the kernel may be incremented, i.e., the kernel may be moved as a sliding window across the data set.

If, at operation 955, the kernel has not moved to the end of the data string generated in operation 920, then control passes back to operation 935 and an average of the new kernel may be determined. Operations 935-950 constitute a loop that effectively "slides" the kernel across the data set. If, at operation 955, the kernel has reached the end of the data string, the control passes to operation 950 and a defect map may be generated. In one embodiment, the defect map may be embodied as a data file that records one or more parameters of the defects detected on the surface of the wafer 710.

Figure 10:
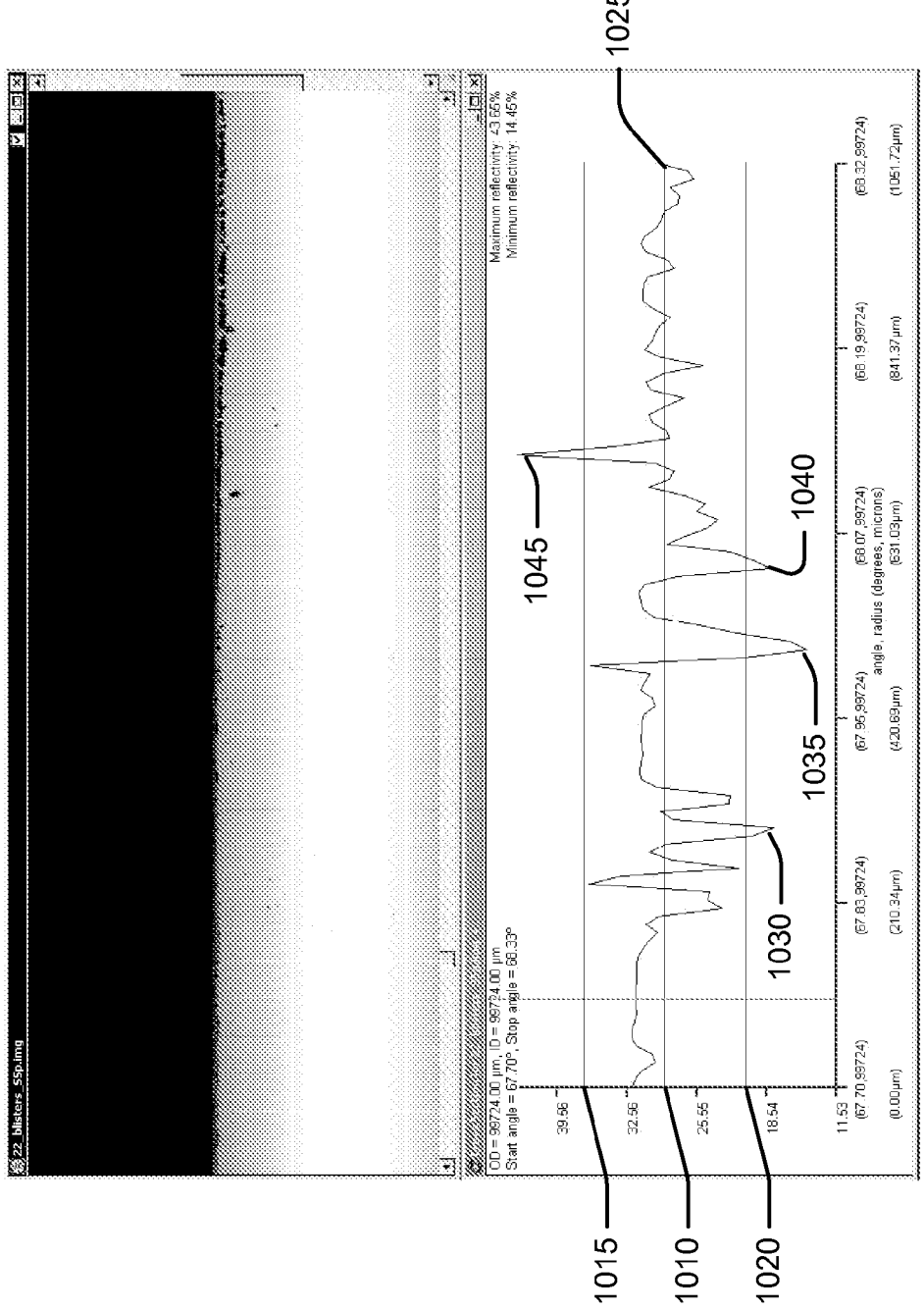
FIG. 10 is a schematic illustration of a portion of a surface of a wafer juxtaposed above a graph illustrating a data set which may be constructed as described in the operations of FIG. 9.

FIG. 10 is a schematic illustration of a portion of a surface of a wafer 710 juxtaposed above a graph illustrating a data set which may be constructed as described in the operations of FIG. 9. The graph depicted in FIG. 10 plots the amount of energy collected from a reflection at a specific data point on a surface of a wafer 710. Referring briefly to FIG. 10, an average (or median) value 1010 may be established that reflects the "background noise" of radiation reflected from the surface of a wafer 710. The data set may then be analyzed to determine an upper threshold 1015 and a lower threshold

1020. The percentage of energy collected from a reflection at a specific point on the surface may then be analyzed to generate a plot 1025 of the data. Data points 1030, 1035, 1040, and 1045 which lie outside the thresholds 1015, 1020, may then be marked as a defect.

Referring back to FIG. 8, at operation 815 the defect shape parameters may be determined from the defect data. In one embodiment the shape parameters may include the area, length, and the aspect ratio of the defect area. At operation 820 one or more signal parameters are determined. In one embodiment the intensity of the reflected radiation is determined from the optical characteristic data associated with each pixel. In another embodiment, the percentage of radiation reflected is determined from the optical characteristic data associated with each pixel.

At operation 825 one or more cross-image parameters may be determined. In one embodiment, cross-image parameters may be determined from data collected contemporaneously, i.e., during the same scan, but having different polarizations. For example, cross-image parameters may be determined between data collected from a single scan comprising both P-polarized and S-polarized (or Q-polarized) light. In another embodiment, cross-image parameter may be determined between data collected at different points in time, in which case the radiation may have the same polarization or a different polarization. Cross-image parameters of interest may include the ratio of amplitudes associated with a defect, the respective areas associated with a defect, the respective dimensions associated with a defect, and the like.

FIG. 11 is a flowchart illustrating operations in one embodiment of a method for determining cross-image parameters. At operation 1110 a first defect map is retrieved. In one embodiment, the first defect map may be embodied as a data file generated as described in operations 810-820. At operation 1115 a first defect is located in the data file. At operation 1120, parameters of first defect are compared to one or more parameters characteristic of representative defects. For example, one or more defect shape parameters associated with the first defect may be compared to shape parameters characteristic of a scratch, a particle, a chip, or the like. If the parameters fail to correspond within a prescribed degree of tolerance, then control passes to operation 1125 and the first defect map is searched for the next defect. If, at operation 1130 another defect is located, then control passes back to operation 1120. If another defect is not located, then the process ends.

If, at operation 1120, parameters of the defect located in the first defect file correspond within a prescribed degree of tolerance to shape parameters characteristic of a scratch, a particle, a chip, or the like, then control passes to operation 1140 and a second defect map is retrieved. At operation 1145 a corresponding region of the second defect map is searched for defects. In one embodiment the second defect map is searched in a region proximate the location in which the first defect was identified. If, at operation 1150, no match is located, then control passes to operation 1160, whereupon if additional defect maps are available, then control passes to operation 1140 and the next defect map is retrieved. If additional defect maps are unavailable, then control passes back to operation 1125 and the first defect map is searched for another defect.

By contrast, if at operation 1145 a defect is located in a corresponding region of the second defect map, then control passes to operation 1160 and one or more cross-image parameters are calculated. In one embodiment, cross-image parameters calculated in operation 1160 may include the ratio of one or more signal amplitudes associated with the defects, a ratio of areas of the defects, a ratio of dimensions associated with the defect, and the like. The cross-image parameters may be stored in a data file and associated with the defects.

Thus, the operations of FIG. 11 form a nested loop in which defects in a first defect map are compared with corresponding defects on a second (or additional) defect maps. Using these operations, a set of cross-image parameters may be constructed.

Referring back to FIG. 8, after the cross-image parameters are determined, the defect(s) may be classified. In one embodiment the system 100 implements a classification system that creates a library of defect classes and compares one or more of the shape parameters generated in operation 815, the signal parameters generated in operation 820, or the cross-image parameters generated in operation 825 with parameters in the library to classify the defects.

At operation 830 one or more defects on the surface of wafer 710 may be classified based, e.g., on one or more of the shape parameters, signal parameters, and the cross-image parameters. At operation 835 information about one or more defects may be reported via a suitable user interface such as, e.g., a display, a printer or the like. In one embodiment defect information may be reported in a user interface that presents a map of the surface of a wafer 710 and locates one or more defects on the surface.

In another embodiment, a system and method for wafer edge inspection may scan the wafer edge with radiation comprising at least two different polarization states. One or more multi-dimensional histograms are generated from data that represents signals from the at least two different polarization states of radiation reflected from points on the surface of the wafer edge. Irregularities in the histogram data may be classified as potential defects, and one or more parameters associated with the potent defects may be determined. Defect regions may be further analyzed, classified, and reported.

Figure 12:
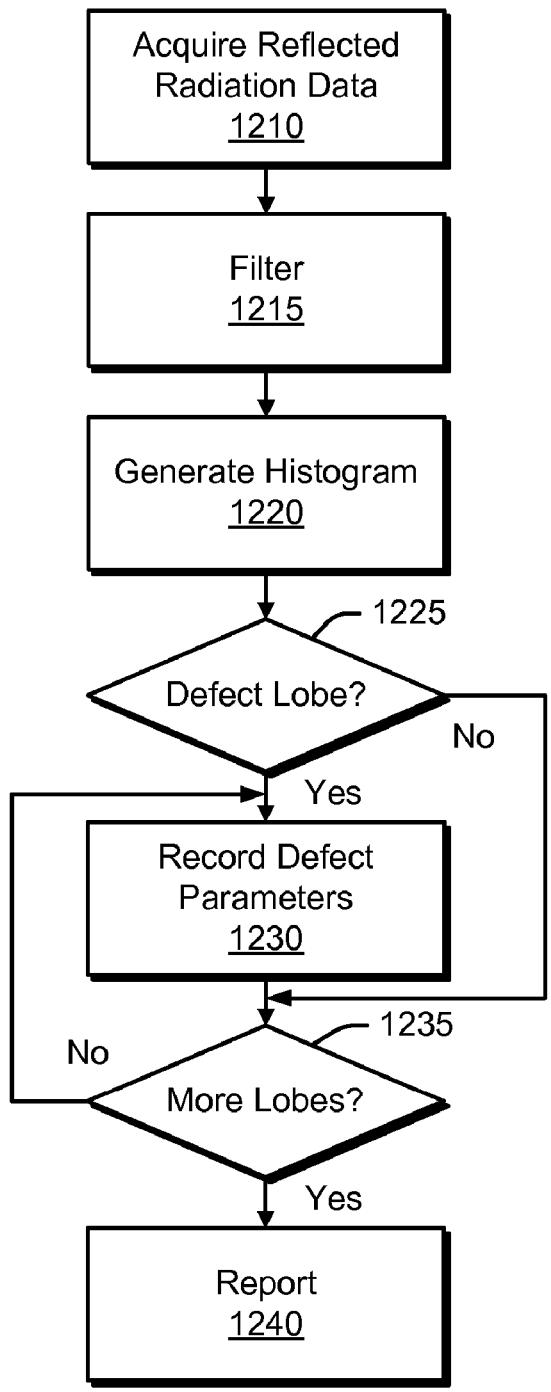
FIG. 12 is a flowchart illustrating operations in another embodiment of a method for determining cross-image parameters.

FIG. 12 is a flowchart illustrating operations in an embodiment of a method for wafer edge inspection. In one embodiment, the operations illustrated in FIG. 12 may be stored as logic instructions in a computer-readable medium such as the memory module 162 depicted in FIG. 1. The memory instructions, when executed by the processor 160, configure the processor to perform the operations depicted in FIG. 12.

Referring to FIG. 12, at 120 reflected radiation data is acquired. In one embodiment, operation 1210 may include scanning the surface of a wafer 710 using a surface scanning assembly as described in FIGS. 1 and 4-6 herein. In one embodiment, the surface scanning assembly is rotated about the edge of the wafer 710 as depicted in FIG. 2. In one embodiment the surface scan may include scanning edge portions of the wafer such as, for example, edge portions 712, 714, 716, 718 and 720.

At operation 1215 the reflected radiation signals may be filtered. In one embodiment, the reflected radiation signals may be filtered using a low-pass filter to remove longer wavelength (i.e., low frequency) reflectivity information. Filtering operations are optional.

At operation 1220 a histogram is generated from the reflected radiation data. In one embodiment, the data acquired in operations 1210-1215 may be stored as discrete data points (or pixels), each of which corresponds to radiation reflected from a specific point on the surface of the wafer 710. In one embodiment, two images (e.g., S and P components of reflected radiation) are acquired and stored.

Next, each S-component pixel is compared to the corresponding pixel of the P-component. A histogram for the combination of reflectivity values is plotted. In one embodiment, reflectivity values from one image make the X-axis of the histogram and the reflectivity values of the other image make the y-axis of the histogram. The counts (frequency) for each combination of values are stored. The histogram may be plotted as shown in FIG. 13.

Figure 13:
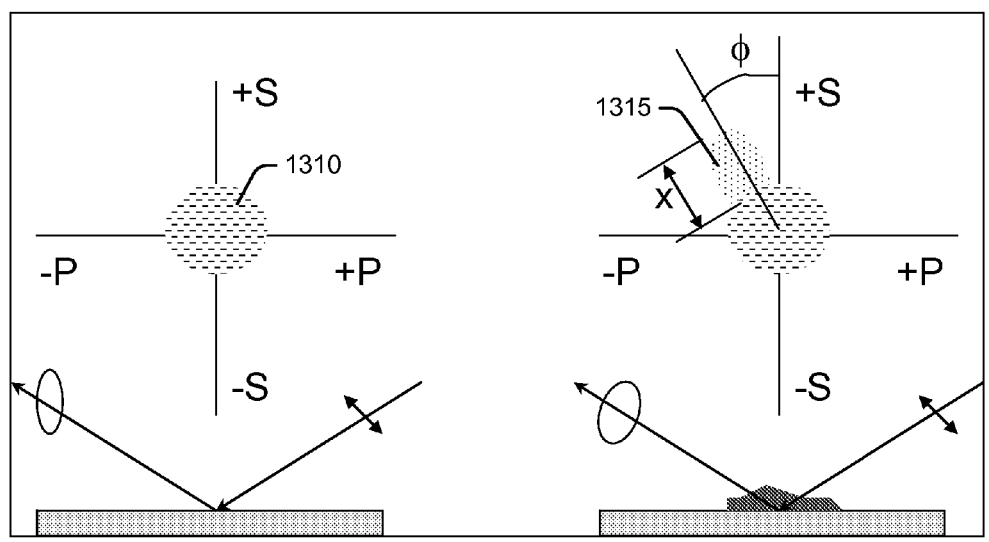
FIG. 13 is a schematic illustration of an inspection environment.

A substrate with a uniform background, without any coatings will have a very tight 2D histogram 1310 as shown on the left of FIG. 13. The incoming linearly polarized radiation will be changed to elliptically polarized light. After subtraction of the average reflectivity from the P and S components of the reflected radiation will be substantially uniformly distributed about a central axis.

By contrast, if there is a film contaminant on the surface (or any material with a different refractive index) incident radiation will be reflected with a different intensity and polarization based on the refractive index of the contaminant, or the material exposed by a defect. The P and S components of the reflected radiation will have a different magnitude and phase when compared to the light reflected from the bare substrate.

When plotted as a two-dimensional histogram, the change in reflectivity may be seen as a deviation from the tight normal distribution 1310 of the background. The deviant data points can be referred to as a 'lobe' 1315. The angle of this lobe with respect to any axis ($\Phi$) and its location in a particular quadrant is a function of the refractive index of the material present on the substrate. The dimension 'x' is a function of the thickness variation of the film.

Multiple alternate techniques for generating two-dimensional histograms are described in U.S. Pat. Nos. 6,268,919, 6,229,610, and 6,130,749, incorporated by reference above.

If, at operation 1225, a defect lobe is detected in the histogram, then control passes to operation 1230 and one or more defect parameters are recorded. In one embodiment, the defect parameters may include the location of the defect, which may be determined by tracing the lobe back to coordinates on the surface of the wafer 710. A technique for tracing the lobe back to coordinates on the surface of a wafer is described in S. Meeks et al., Optical Surface Analysis of the Head-Disk-Interface of Thin Film Disks, ASME Transactions on Tribology, Vol. 117, pp. 112-118, (January 1995), which is incorporated by reference herein in its entirety. Additional defect parameters may include shape and or signal parameters as described above. If, at operation 1235 there are additional lobes, then control passes to operation 1230 and additional defect parameters may be recorded. Operations 1230-1235 may be repeated until, at operation 1235, there are no further lobes to analyze, whereupon control passes to operation 1240 and the defects may be reported. In one embodiment, one or more defects may be reported via a suitable user interface such as, e.g., a display, a printer or the like. In one embodiment defect information may be reported in a user interface that presents a map of the surface of a wafer 710 and locates one or more defects on the surface.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A system to rotate an optical head around an edge of a wafer, comprising:
   a radial motor to move the optical head in a first radial direction across a surface of the wafer and also in a second radial direction opposite the first radial directional across an opposing bottom of the wafer;
   a rotational motor to move the optical head around the edge of the wafer such that the optical head first faces the surface of the wafer and then rotates around the edge to face the bottom of the wafer; and
   a sensor to measure a distance between the optical head and an underlying one of the surface, edge, and bottom of the wafer;
   wherein the radial motor and the rotational motor cooperate to maintain a constant distance between the optical head and the underlying one of the surface, edge, and bottom of the wafer as the optical head moves around the edge of the wafer.

2. The system of claim 1, further comprising a third motor to rotate the wafer about an axis perpendicular to the surface.

3. The system of claim 1, further comprising:
   a radiation targeting assembly to target radiation onto the surface and the edge; and
   a reflected radiation collecting assembly to collect radiation reflected from the surface and the edge.

4. The system of claim 3, further comprising:
   a signal processing module to generate surface parameter data from the reflected radiation;
   a defect detection module to analyze the surface parameter data to detect a defect on the surface.

5. The system of claim 3, wherein the reflected radiation collecting assembly comprises a curved collecting mirror to collect reflected radiation.

6. The system of claim 5, further comprising at least one of a paraboloid collecting mirror, an ellipsoidal collecting mirror, or a spherical collecting mirror.

7. The system of claim 4, wherein the signal processing module generates a reflectance data set that correlates one or more reflectance values of the reflected radiation with one or more locations on the surface.

8. The system of claim 3, wherein the radiation comprises at least one of a S polarization, a P polarization, or a Q polarization.

9. The system of claim 3, wherein the incident radiation comprises at least one of circular polarization or elliptical polarization.

10. The system of claim 4, wherein the defect detection module:
    establishes a background noise level of reflectance values from the reflectance data set;
    establishes one or more thresholds in variation from the background noise level; and
    designates as a defect one or more points in the data set having reflectance values outside the one or more thresholds.

11. The system of claim 4, wherein the signal processing module further generates a two dimensional histogram that correlates one or more reflectance values of the reflected radiation with one or more locations on the surface.

12. The system of claim 11, wherein the defect detection module analyzes the two dimensional histogram to locate one or more defects on the surface.

13. The system of claim 4, further comprising a presentation module to present defect information to a user via a user interface.

14. The system of claim 4, further comprising a scattered radiation collecting assembly that collects radiation scattered from the surface, wherein the scattered radiation collecting assembly comprises at least a detector to collect scattered radiation from the surface.

15. The system of claim 1, wherein the wafer is stationary as a rotational motor moves the optical head around the edge of the wafer.

16. the system of claim 1, wherein the edge of the wafer is not in the shape of a semicircle.

17. The system of claim 3, wherein the wafer is stationary during radiation collection.

18. the system of claim 3, wherein the edge of the wafer is not in the shape of a semicircle.

19. The system of claim 3, wherein the radiation targeting assembly comprises:
   polarizing device;
   a laser diode; and
   a focusing lens.

20. The system of claim 19, wherein the polarizing device further comprises transmitting at least one of a S polarized, a P polarized, or a Q polarized light.

21. The system of claim 20, wherein the reflected radiation collecting assembly collects at least one of a S polarized, a P polarized, or a Q polarized light.

22. The system of claim 21 wherein the reflected radiation collecting assembly further comprises a low-pass filter to remove wavelength length larger than a set threshold value.

23. The system of claim 3 wherein the reflected radiation collecting assembly further comprises a low-pass filter to remove wavelength length larger than a set threshold value.

24. The system of claim 19, wherein the polarizing device further comprises transmitting two different polarized states of light.

25. The system of claim 3, wherein:
   the radiation targeting assembly further comprises transmitting two different polarized states of light; and
   the reflected radiation collecting assembly collects the two different polarized states of light.

26. The system of claim 3, wherein the reflected radiation collecting assembly comprises:
   a collimating lens;
   a wobble reduction lens;
   a quarter wave plate;
   a Wollaston prism rotated at 45 degrees to the plane of incidence; and
   at least one detector.

27. The system of claim 26, wherein the at least one detector comprises two detectors, wherein the two detectors comprise either quadrant detectors or PIN photodetectors.

28. The system of claim 26, wherein the wobble reduction lens is a converging lens positioned such that the wobble reduction lens' focus length is substantially equal to the distance between the wobble reduction lens and the at least one detector.

29. The system of claim 1, further comprising:
   the radiation targeting assembly to target a second surface, wherein the second surface is different than the surface; and
   the reflected radiation collecting assembly to collect radiation reflected from the second surface.

* * * * *